United States Patent [19] … [11] Patent Number: 5,014,377
Dixon … [45] Date of Patent: May 14, 1991

[54] PILLOW

[75] Inventor: Linda H. Dixon, Laurel, Calif.

[73] Assignee: E. R. Carpenter Company Inc., Richmond, Va.

[21] Appl. No.: 542,810

[22] Filed: Jun. 22, 1990

Related U.S. Application Data

[63] Continuation of Ser. No. 190,847, May 6, 1988, abandoned.

[51] Int. Cl.⁵ ............................................. A47C 20/02
[52] U.S. Cl. .......................................... 5/434; 5/446
[58] Field of Search ................... 5/431, 434, 435, 436, 5/437, 481

[56] References Cited

U.S. PATENT DOCUMENTS

| | | | |
|---|---|---|---|
| D. 207,079 | 2/1967 | Wirth . | |
| D. 254,029 | 1/1980 | Barbagallo . | |
| D. 276,938 | 12/1984 | Pedersen . | |
| 2,700,779 | 2/1955 | Tolkowsky | 5/434 X |
| 2,940,088 | 2/1959 | Boos . | |
| 3,347,544 | 3/1965 | Uffenorde . | |
| 3,360,548 | 4/1965 | Moore et al. . | |
| 3,482,571 | 10/1967 | Behrendt . | |
| 3,648,308 | 3/1972 | Greenawalt | 5/436 |
| 3,694,831 | 10/1972 | Treace . | |
| 3,757,364 | 9/1973 | Downing | 5/436 X |
| 4,070,719 | 1/1978 | Morgan | 5/481 |
| 4,186,738 | 2/1980 | Schleicher et al. . | |
| 4,218,792 | 8/1980 | Kogan | 5/436 |
| 4,259,757 | 4/1981 | Watson . | |
| 4,320,543 | 3/1982 | Dixon | 5/434 |
| 4,432,107 | 2/1984 | Clark et al. | 5/434 X |
| 4,494,261 | 1/1985 | Morrow | 5/434 X |
| 4,748,702 | 6/1988 | Sandler | 5/434 |
| 4,754,513 | 7/1988 | Rinz | 5/434 X |
| 4,773,107 | 9/1988 | Josefek | 5/434 |
| 4,805,603 | 2/1989 | Cumberland | 5/436 |
| 4,816,494 | 3/1989 | Watson, Jr. et al. . | |
| 4,829,614 | 5/1989 | Harper | 5/436 |

FOREIGN PATENT DOCUMENTS

| | | | |
|---|---|---|---|
| 270014 | 6/1988 | European Pat. Off. | 5/434 |
| 477526 | 8/1956 | Fed. Rep. of Germany . | |
| 2305956 | 10/1976 | France | 5/434 |
| 2573972 | 6/1986 | France | 5/434 |

OTHER PUBLICATIONS

ProPillow (TM) product information brochure, (1981).
Silent Knight Pillow advertisements one of which appeared in USA Today Newspaper on Nov. 11, 1987.
Thera-P Anti-Snoring Cradle Pillow product brochure.
Slumber Cushion II product information brochure, (1987).

Primary Examiner—Gary L. Smith
Assistant Examiner—Michael J. Milano
Attorney, Agent, or Firm—Beveridge, DeGrandi & Weilacher

[57] ABSTRACT

An anti-snoring pillow which reduces the snoring by the user when sleeping by positioning the head of the user such that the degree of blockage in the user's breathing passageway is reduced. The anti-snoring pillow includes a base member which is preferably inclined and has a curved front edge which is lower in height than the rear edge. The upper surface of the base member adjacent the front edge has an elongated bolster secured thereto, which bolster is curved along its length to conform to the curved shape of the front edge of the base member. The bolster also includes a curved peripheral cross-sectional area for comfortable support of a user's neck. The bolster and the base member, and the choice of materials therefor act in conjunction to ensure comfort and also the positioning of a user's head so as to decrease the blockage of the user's breathing passageway when the user is in a back or in a side sleeping position.

34 Claims, 8 Drawing Sheets

PILLOW

This application is a continuation of application Ser. No. 190,847, filed May 6, 1988, now abandoned.

BACKGROUND OF THE INVENTION

This invention relates to a pillow suitable for the prevention and/or reduction of snoring. More particularly, this invention relates to a pillow which optimizes the user's breathing passageways by proper head, neck and shoulder positioning.

The problems associated with snoring have been with us since the beginning of time and yet little has been done to properly confront these problems. It is estimated that, in the United States alone, there exists about 10 million "heavy" snorers whose "log sawing" at night tends to cause irritation and long sleepless nights for those who are unlucky enough to be subjected to the snoring. In addition, snoring, especially heavy snoring, presents to the snorer potential health hazards as snoring decreases the amount of oxygen reaching the blood stream. Moreover, it is estimated that about 86% of the male population and 57% of the female population snore to some degree while sleeping; thus, it is evident that the problems associated with snoring effect virtually everyone in some way or another.

Social snoring is a term coined to define the situation where the one that is snoring is not alone. In such situations it is estimated that 15% of men and 52% of women are bothered to some extent by the snoring of another. Social problems are likely to arise in such an environment and it is well documented that snoring is one of the major causes for marital problems. In fact, as a well known advice columnist once stated, "love may be blind, but it is not deaf." A spouse or sleeping partner being subjected to another's snoring night after night loses sleep and inevitably becomes tired and irritable with the irritability being yet another factor which can create friction in a marital setting. A not unusual chain of events for a person placed in such a situation is to first attempt to solve the problem by poking or rolling the snoring partner. Attempts of this sort are usually ineffective and, if effective, only temporary in nature. Hence, the sleeping partner's next step is usually to refuse to sleep in the same room. Finally, in the more aggravated situations, the sleeping partner will refuse to sleep in the same house with divorce being one way of achieving such a goal.

Snoring is an indication that the breathing passageways of the individual snoring are partially blocked. The partial blockage of the breathing passageways during snoring means less oxygen is reaching the blood system and thus there is a greater chance that the individual will be subject to health problems such as heart attacks, strokes and hypertension, all of which are related to the amount of oxygen in the blood stream. Sleep Apnea, a severe snoring disorder where a victim chokes hundreds of times a night, represents even a more severe health hazard which can lead to the above health problems as well as daytime drowsiness and even narcolepsy in the more severe cases.

The causes for snoring include, among other, tongue obstruction (hypopharynx); nasal obstruction (colds, broken nose, etc.); excessive soft palate tissue; pharyngeal narrowing or elasticity; the presence of enlarged tonsils and/or adenoids; and sleep posture.

As the problems associated with snoring are so acute, various articles have been placed on the market in an attempt to provide solutions. These articles have proven to both vary in price, comfort and effectiveness. For instance, articles placed on the market to confront the problems associated with snoring include: (1) indicators which indicate when the sleeper has moved to his back—a position that leads to increased snoring; (2) tongue retaining devices; (3) elastic masks and splints to keep the mouth open; (4) various drugs which stimulate those portions of the body inducive to snoring; (5) expensive forced air machines; and (6) modified pillow shapes.

The foregoing articles known in the prior art have not proven entirely satisfactory to those suffering the plight of snoring. The inadequacies of the prior art result from, among other things, in their being either too expensive, too uncomfortable, ineffective or any combination of the same.

OBJECTS OF THE INvENTION

An object of the present invention is to provide a pillow which, inter alia, solves or at least reduces the aforementioned problems. That is, an object of the present invention is to provide an anti-snoring pillow which is effective in reducing or preventing snoring, and which is comfortable, yet inexpensive to manufacture. Also, by providing such a pillow, the present invention inherently achieves solutions to the previously discussed problems associated with "social snoring".

In achieving such objectives, the present invention utilizes a novel design which provides for optimal breathing passageways for the user while sleeping. The optimal breathing passageways are achieved by proper positioning of the user's head, neck and shoulders. Furthermore, optimization of the breathing passageways is achieved without reducing the comfort level of the user. Rather, the present invention provides a high degree of comfort for both back and side sleepers.

The amount of reduction in snoring depends, to a large extent, on which of the aforementioned factors are causing the snoring. It is clear, though, that by proper positioning of the head and the maintaining of optimal breathing passageways, many of the factors leading to snoring can be reduced if not eliminated entirely.

Generally, those who are problem snorers are those who sleep on their back or on their side, with those sleeping on their back usually being somewhat noisier than those sleeping on their side. This observation is illustrative of the fact that the position of a person's breathing passageways is an important factor in whether and to what degree a person will snore. Therefore, sleep posture can be said to play a role in either aggravating or lessening the severity of snoring. The present invention is directed at providing a comfortable pillow and a pillow which will ensure optimal breathing passageways so as to reduce snoring for both those who sleep on their back and those who sleep on their side.

Basically, snoring can occur due to a partial obstruction at each or a combination of the following:

(1) Nasal—This is often due to nasal obstruction from polyps, a deviated septum, allergies or a common cold. These causes, for the most part, are only correctable by surgery or, as in the case of a cold, are temporary.

(2) Nasopharynx—Individuals having relatively large amounts of soft tissue (or more easily extendable soft tissue) at the back of their mouth where the "soft palate" or uvula meets the back of the throat (the area referred to as the nasopharynx) are likely to have snoring problems. This area, comprising the uvula and soft palate and pharyngeal folds, vibrates or flutters during breathing and can cause a sound loud enough to even awaken a sound sleeper.

(3) Hypopharynx—This third area of the airway is the area at the back of the mouth where the tongue meets the pharynx. In order to keep the tongue from falling backward and blocking the airway, it is helpful to thrust the jaw forward. Since the tongue is connected to the jaw, the thrusting forward of the jaw tends to keep the relaxed tongue from partially or completely blocking the back of the throat.

In addition, it has been determined that the position of one's jaw with respect to one's clavicle has an effect on the clearness of one's breathing passageways. When the jaw is placed close to one's chest or clavicle area, the breathing passageways become less clear. This position of the jaw leads to narrowing or constriction of the airway and an increase in snoring. Additionally, when the jaw is moved too far from ones chest (i.e., head tilted back to a great extent), the breathing passageways become less clear. This positioning of the head induces the hypopharynx to move to a partially blocked position and increases the chances of the relaxed tongue curling back and creating blockage. A position of the head between these extremes has been found to lead to an optimization of a person's breathing passageways. More specifically the head should be positioned such that the neck is pushed outwardly and the head curled back a bit such that the bottom surface of the chin lies virtually in the same plane as the upper surface of the neck.

Moreover, a twisting of the head while the rest of the body remains stationary tends to create a narrowing or a reduction in the area of the breathing passageways. Thus a person lying on his back with his head twisted to one side will not have as clear passageways as one having his head untwisted. Also, a person lying on his side would have partially blocked breathing passageways when the head is twisted down towards the sleeping surface.

Accordingly, it can be seen that the position of a person's head while sleeping plays an important role in how clear the person's breathing passageways are. Furthermore, as there is a correlation between the clearness of one's breathing passageways and the presence of snoring, sleep posture can tend to aggravate or lessen the severity of snoring.

SUMMARY OF THE INVENTION

To accomplish proper sleeping position of the head, the present invention utilizes a pillow structure which places the head such that the bottom surface of the head is at or below the bottom surface of the neck. Also to obtain optimal breathing passageways the neck and head are placed in an extended or "sniffing" position where the breathing passageways are aligned and remain essentially optimally open whether the person is on his back or side. The pillow structure also acts to prevent twisting of the head when the person is lying on his back or side.

In so achieving the proper sleeping position for the head of the user, the pillow includes a base member which preferably is at an incline with the forward edge of the base member being lesser in height than the back edge. A bolster member is secured to the top of the base member adjacent the forward or front edge of the base member. The bolster is curved such that its central section is closer to the back edge of the base member than are the end sections of the bolster. The bolster also has a peripheral cross-sectional area which is generally curved in shape. In a preferred embodiment, the pillow also includes a convoluted laminate layer which is secured to the upper surface of the base member or, alternatively, has a convoluted surface formed directly in the upper surface of the base member.

Furthermore, in one embodiment of the invention, the upper surface of the base member has formed therein a depression which is positioned generally midway between the two sides of the base member. The depression preferably has a boundary edge positioned directly behind the inner-most portion of the bolster and extends rearwardly toward the rear edge of the base member so as to create a relatively small vertically extending depression in the base member. The depression is preferably formed so as to conform to the back of the head of the user.

The convoluted surface extending from the base member is preferably in what is termed a "hill and valley" design. Moreover, the generally curved cross-sectional exterior surface of the bolster preferably is sculptured so as to have a scallop shape. The sculpturing of the exterior surface of the bolster leads to the formation of a plurality of ridges and grooves which extend along the length of the bolster. These ridges and grooves assist in maintaining the person's head in position by preventing undue movement. Moreover, the ridges and grooves lead to greater comfort as much of the weight of the head and neck is dispersed along the larger convoluted surface area at or behind the bolster rather than straight down. That is, by having the hills "squash" outwardly at their base the weight of the head is better distributed over the upper surface of the pillow and there is less of a localized vertical upward force acting against the head. Convoluted surfaces for pillows and methods for forming pillows with convoluted surfaces are known, as may be seen from applicant's U.S. Pat. No. 4,320,543, whose teaching is incorporated herein by reference.

The specific shape of the bolster and the base member (with or without a convoluted laminate layer) acts to ensure proper positioning of the person's head while sleeping. The bolster's cross-sectional surface, which is generally curved in shape, is designed to nestle under and support a person's neck. The bolster also acts to provide some support to the lower part of the head of the user when the user is resting on his back. Further, the bolster's cross-sectional shape is designed such that a person resting on his side will have the side of his face in the region of the chin essentially lying on a plane which is parallel to the surface supporting the pillow (i.e., the bed). The bolster's longitudinal or lengthwise curvature together with the front edge of the base member provide a concavity which enables the shoulders of a user to be properly positioned relative to the pillow. This is true whether the user is sleeping on his back or on his side, since the curvature and length of the pillow are designed to accommodate the natural downward slope of both shoulders or just a single shoulder.

In an embodiment which includes a recess for the head in the upper surface of its base member, there is provided a region into which the major portion of the back of the head of the sleeping person is nested when in the back sleeping position. Also, for the side sleeping position, the recess is positioned such that the wider portion of one's face is within the recess and the thinner chin portion is lying on the top innermost edge of the bolster to keep the jaw forward.

The choice of material or materials being utilized to form, the base member, bolster and convoluted upper surface is chosen so as to coordinate with the geometry of the pillow such that the optimal airway is achieved. That is, a person sleeping on his side has his head positioned such that a plane parallel to the surface supporting the pillow and body, which is at the level of a person's spinal cord, would bisect the person's head. Also, the plane is positioned so as to bisect the person's nose which would indicate that the head is not twisted.

On the other hand, for a person lying on his back, the head is positioned such that a plane passing through the bottom surface of the chin and being substantially parallel to the neck's upper surface which is both extended along its length and forced upwardly away from the pillow supporting surface by the bolster, intersects the plane of the supporting surface of the pillow at an obtuse angle. In such a position, a second plane extending through the tip of the nose and being parallel to the aforementioned plane also traverses the plane including the support surface of the pillow at an angle which is obtuse with the supporting surface for the pillow. Moreover, the head is positioned such that at its lowest point it is about 5-20 cms above the pillow supporting surface or even more preferably about 8-10 cms above the pillow supporting surface. Also, the bottom surface of the center portion of the neck is generally about 2-5 cms higher from the supporting surface for the pillow than is the lowest point of the head.

The specific geometry of the present invention, as well as the coordinated use of the different materials used in making the pillow enables a person to sleep comfortably while experiencing a reduction in snoring.

Other advantages and improvements over the prior art will become more apparent from the description made hereinbelow with reference to the accompanying drawings in which.

DETAILED DESCRIPTION OF THE DRAWINGS

Figure 1:
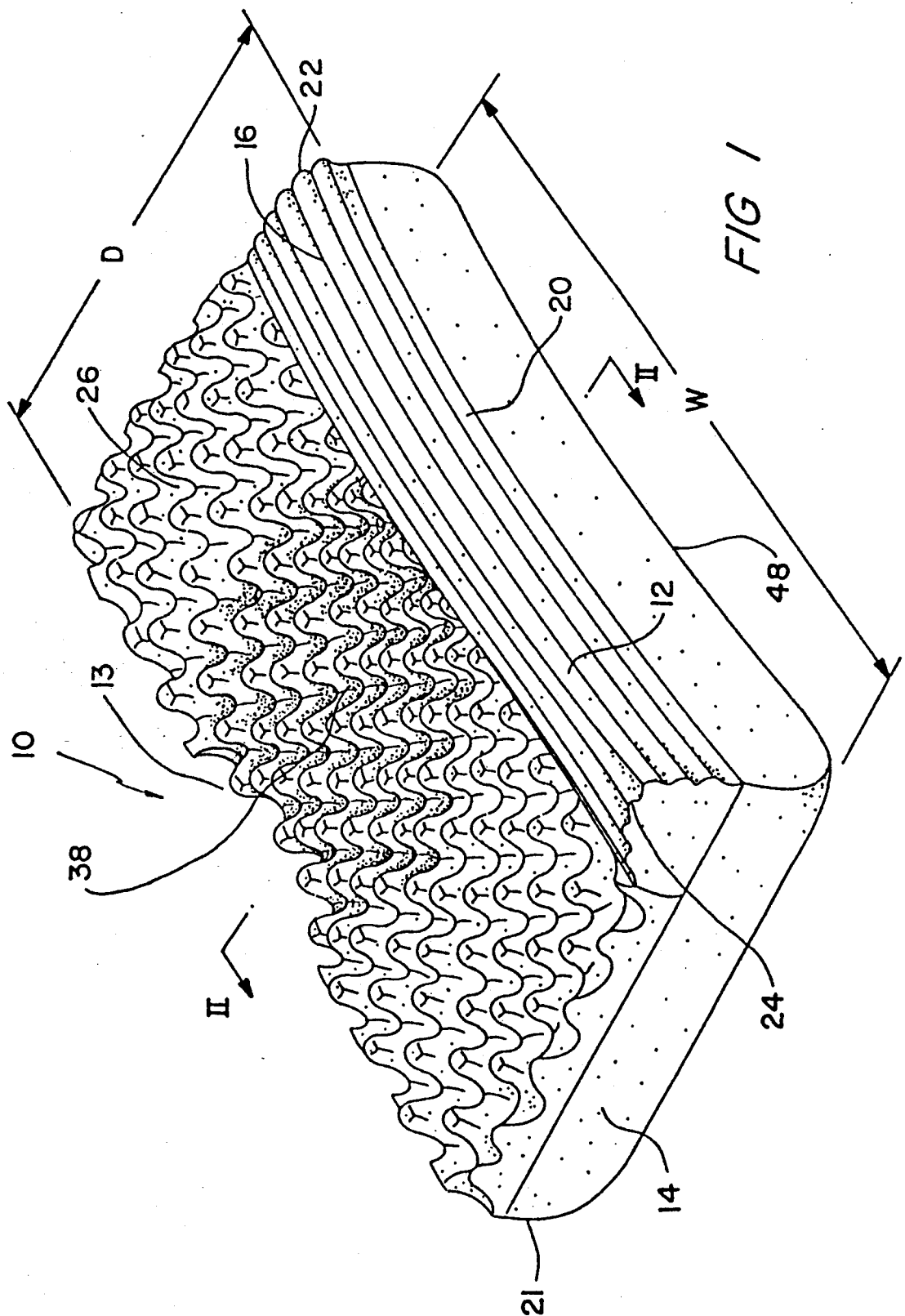
FIG. 1 represents a perspective view of one embodiment of the pillow of the present invention.
Figure 2:
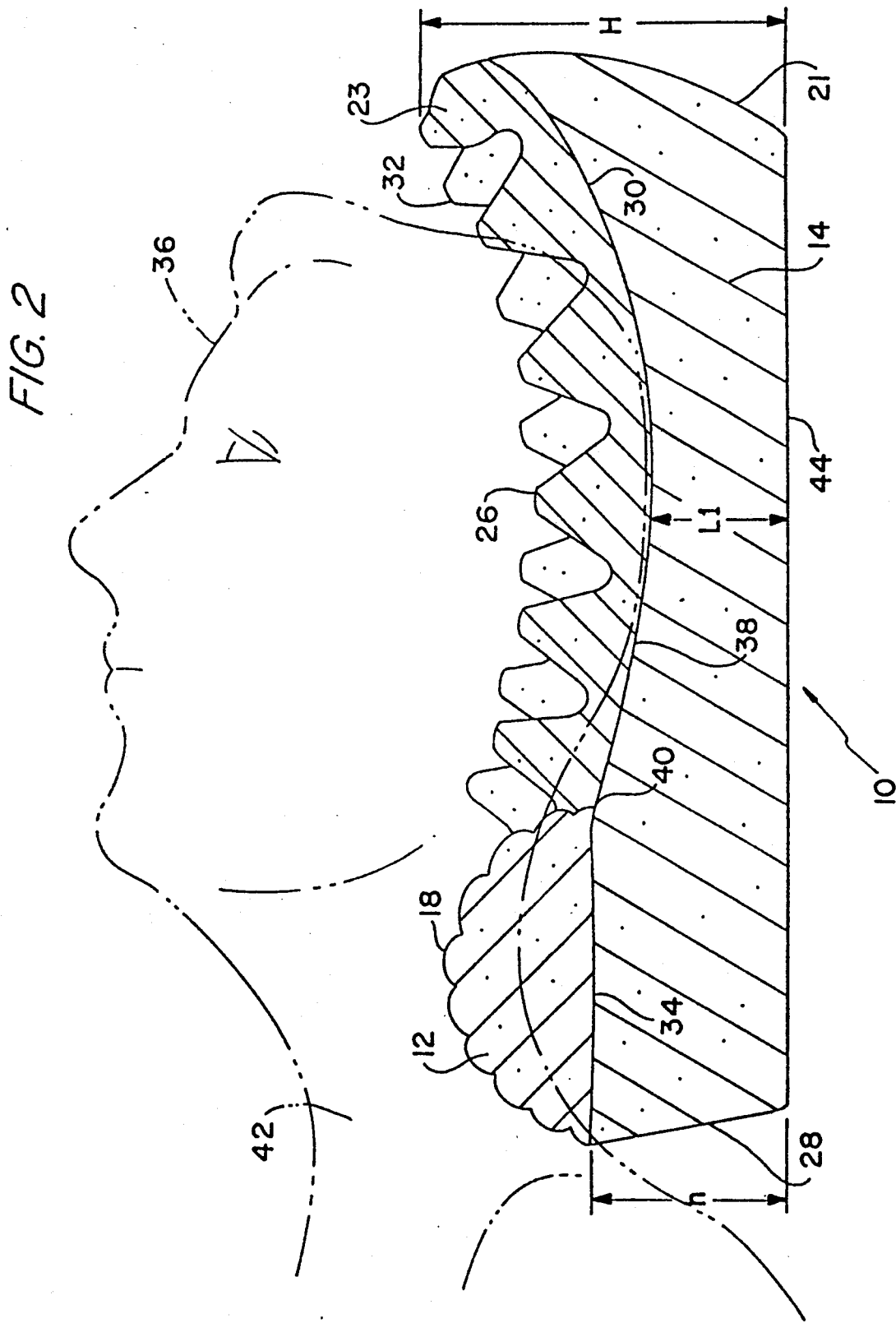
FIG. 2 represents a cross-sectional view along the lines II—II of FIG. 1.

FIG. 1 shows a perspective plan view of a preferred embodiment of the present invention. FIG. 1 illustrates an anti-snoring pillow 10 having a bolster 12 secured to the upper surface of base member 14 along one edge of the latter. The bolster 12 has a generally curved outer surface 16 which has contoured therein a plurality of essentially parallel ribs or scallops (18, FIG. 2). Further, the bolster 12 is curved along its length such that its center portion 20 is disposed closer to the back edge 21 of the base member 14 than are the two ends 22 and 24 of the bolster. In addition, the bolster is shown to have essentially the same vertical thickness over its entire length. As seen in FIG. 2, the bolster 12 is hemispherical in cross-section and can be initially made with a substantially cylindrical configuration which, when cut into essentially two equal halves or hemispheres and subsequently trimmed to the proper dimensions, is securely affixed to the upper surface adjacent the front end of the base member 14.

FIG. 1 also reveals a convolute surface 26 which is integrally attached to the base member 14 either by forming the convolutions directly in the base member or as a separate layer of convoluted material laminated onto the upper surface of the base member 14.

FIG. 2 illustrates a cross sectional view along lines II—II in the embodiment of the pillow of FIG. 1. Bolster 12 is depicted as being a separate element as with respect to base member 14 and the convoluted layer 23, with all three components being adhesively or otherwise secured together, as is well known in the art. It is also contemplated that the bolster 12 and the base member 14 and the convoluted layer 32 can be formed as a unitary, integral body. As can be seen in FIG. 2, the upper surface 30 of the base member is inclined with its back edge 21 having a height "H" which is greater than the height "h" of front edge 28. In a preferred embodiment height "H" is about 2-5 times the height of "h". For instance, in one preferred embodiment, the height "H" is about five inches while the height "h" is about two inches. In addition, the depth "D" of the pillow is about twenty inches while the width "W" (FIG. 1) of the base member 14 is about twenty-two inches. These measurements as well as the amount of incline, if any, are variable, with the ultimate goal being the proper positioning of the user's head as will be explained more fully hereafter. A preferred range of incline from the horizontal includes a range of 5° to 25°.

FIG. 2 also illustrates the convolute surface 26 being provided by securing a layer of convoluted material 32 onto the upper surface 30 of base member 14. Securement of the bolster can be achieved by attaching the bottom edge 34 of bolster 12 to the upper surface of base member 14. Securement of both the convolute material 32 and the bolster can be achieved by utilizing an adhesive or any other conventional type of bonding means known in the art. Alternatively, it is possible, depending on the manufacturing technique, to form the bolster, base member and convoluted surface from a single piece of material.

The bolster 12 is preferably semi-circular in shape and is attached to the upper surface of the base member 14 as depicted in FIG. 2. Various other shapes could also be utilized provided the shape achieves a proper positioning of the head and a high degree of comfort. In a preferred embodiment, the radius of the semi-circular bolster ranges from about 1.5 to 4 inches and more preferably about 2-4 inches and even more preferably the radius of the bolster is about 2.5 inches. In addition, the longitudinal length of the bolster is preferably slightly longer than the front edge length of the base member 14. For instance, with a front edge of about 22 inches, the curved bolster would preferably have a length of about 22.75 inches. In a preferred embodiment the vertical thickness of the bolster is constant over its entire length. In another embodiment there is contemplated forming a slight dip in the bolster's vertical thickness near the center portion where the neck of the user will be supported.

In a preferred embodiment of the invention the bolster 12, the layer of convolute material 32 and base member 14 are all formed of a cellular polyurethane material. While the polyurethane can be the same for each component of the pillow, it is preferred that each component be made of a different cellular polyurethane. A densified polyurethane material sold under the trademark OMALUX, by E. R. Carpenter Company, Inc. has proven to be adequate for the purposes of the present invention especially with regard to the bolster material. It is also possible to form one or more components of the anti-snoring pillow of the invention of other material or combinations of other material such as, but not limited to, goose down, air or liquid filled compartments, natural or synthetic fibers including hollow fill tubed fibers, or the like.

The firmness of the material being used is also variable. Nonetheless, as will be explained more fully hereafter, it is important to maintain the firmness of each of the three components at a value which will achieve a head position that provides the user with optimal breathing passageways.

The weight of a human's head is said to generally range between ten and fourteen pounds. Consequently, it is important to provide the material with a firmness which is well suited for handling such a weight—a feature which is lacking in many of the prior art pillows. Referring again to FIG. 2, a human head 36 is depicted in dot-dash lines. Again, as the weight of the head normally varies between ten to fourteen pounds, it is important to pick a material having an adequate firmness or ILD value. The ILD firmness value represents the amount of displacement one can expect in a material when a weight acts thereon to compress the material. For instance, an ILD value of 14 would mean that a weight of 14 pounds would displace a four inch thick piece of the material one inch. Similarly, a 12 pound weight would displace a four inch thick piece of material having an ILD value of 12 by one inch.

In a preferred embodiment, the ILD value for the anti-snoring pillow ranges between 6 to 25 and, more preferably, between 10 and 21. It has also been found an advantage to vary somewhat the firmness value for each of the component parts of the anti-snoring pillow (i.e., the bolster 12, base member 14 and/or convoluted material 32). Specifically, it has been determined advantageous for the purposes of the pillow of the invention to have the firmness value of the bolster 12 to be initially lower than the initial firmness value for the base member 14 and/or convoluted surface 32, such as, for example, an ILD value of 14 for the bolster, and an ILD value of 18 for the base member and an ILD value of 21 for the convoluted material for the first 25% of compression of the material.

Additionally, it has proven advantageous to form the bolster member of a cellular polyurethane foam having a higher density value then that of the base member. In such a case, if the bolster were to have an initial ILD value of about 11 and the base member an initial ILD value of 16, than it would be easier to compress the bolster member than the base member. However, upon further compression of the material the denser material becomes more difficult to compress than the less dense base member material. Therefore, in a region of 25% compression or more the ILD values reverse and it becomes more and more difficult to compress the denser material. This feature provides added comfort in the neck of a user as it is the neck which is being extended or "stretched" upwardly away from the supporting surface of the pillow. Comfort is enhanced because the initially less firm bolster 12 provides a soft surface for the neck. However, firm support on the neck is also required to prevent straining of the neck in its extended position. This firm support is provided as the denser bolster is compressed by the user.

FIG. 1, and more specifically FIG. 2, show a preferred embodiment of the invention having a depression 38 formed in the upper surface of base member 14. Depression 38 is generally shaped to conform to the back of the head of a user 36 once the head is placed within the depression. That is, the depression is formed such that the deepest portion of the depression supports the base of the head and the shallower edge portion 40 surrounding the forward part of depression 38 supports that area of the head 36 nearest the neck 42. In addition, the shallow portion 40 of the depression 38 is positioned just inwardly of the innermost edge of the bolster 12 such that there is maintained a smooth and comfortable transition from the bolster 12 to the base member 14. A depth which has proven adequate for the purposes of the invention is one which at its deepest point in base member 14 is between about 1 and 4 inches and more preferably about 2.6. The deepest portion of the depression 38 and the firmness and density of the material for the base member 14 and of the convoluted material 32 are such that the head of an average person (i.e., about 12 pounds) would be positioned such that the lowermost portion of the head would be at a height L1 above the bottom edge 44 of the base member 14 (FIG. 2). Height L1 in base member 14 is preferably about 3 to 5 inches, and, more preferably, in the range of about 3.5 to 4 inches. The depression 38 is also of a depth sufficient to ensure that the lowest part of the head supported therein is lower than the area of the neck which is supported by the bolster 12.

Figure 5:
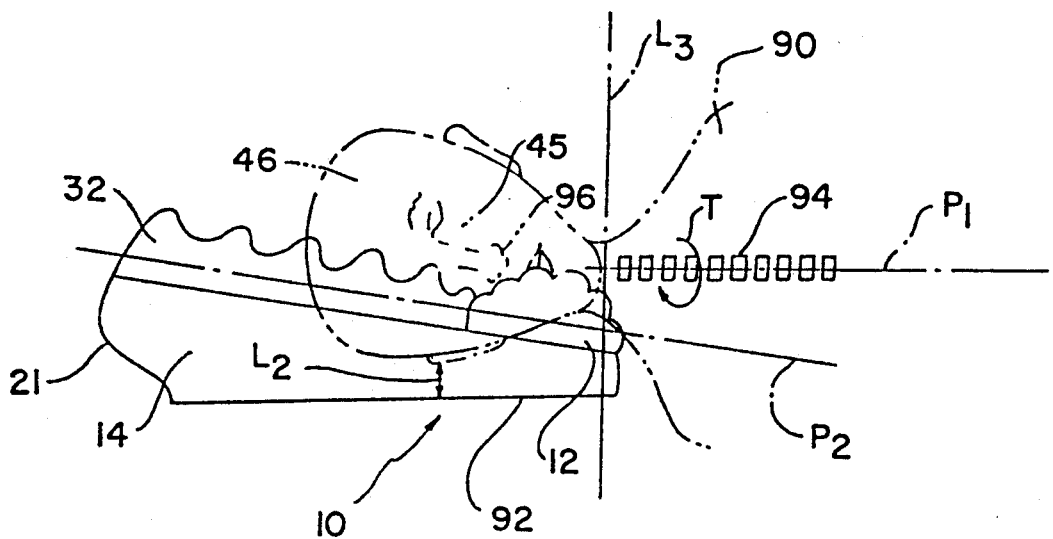
FIG. 5 represents a side view of the invention as well as the position of the head and neck of a user in a side sleeping position.

Referring once again to FIGS. 1 and 2, the scalloped or ribbed surface 18 of bolster 12 is provided with a plurality of ridges and grooves extending along the longitudinal length of the bolster. As illustrated in FIG. 5, the scalloped surface 18 of bolster 12 provides a means for helping to prevent the sliding of the face 45 of user 46 away from the bolster. This is achieved, in part, by having the soft portions of the user's face disposed somewhat within the grooves formed by scalloped surface 18. In addition, like the convoluted surface, the scalloped surface provides a more comfortable surface for supporting the neck and a portion of the face and further provides a surface which radiates the body heat more efficiently. The comfort of the surface of the bolster is attributable, in part, to its ability to disperse the weight of the head horizontally as well as vertically.

As illustrated in FIG. 1 and in FIGS. 3A–3D, the curved surface 48 of the pillow and the bolster comprises a central portion 20 and end portions 22 and 24 of the bolster and that portion of the base member disposed below it. The curved surface of the bolster 12 has a radius R which preferably is within the range of about 1.5 to 3 feet and, more preferably, about 2.5 feet. The arc of curved surface 48 is small enough to avoid any undue abutment between a user's shoulders when in the back sleeping position (as depicted in FIGS. 2 and 4) and the bolster and the end of the pillow. The curved surface is of a shape which generally matches the contoured or inclined slope of a user's shoulders. This shaping of the front edge thus provides a slight abutment between the shoulders and the front edge which assists in preventing the pillow from becoming out of position with respect to a user, especially a back sleeper.

Furthermore, the curved surface 48 of the pillow and bolster 12 permits a user sleeping on his side (FIG. 5) to position the lower neck and shoulder within the central area of the arcuate end of the pillow in a manner which ensures added comfort as well as proper support for the head and neck. While it would be possible in certain situations to utilize a straight edge bolster, the preferred embodiments of the present invention utilize a curved bolster having the advantages noted above.

Figure 3A:
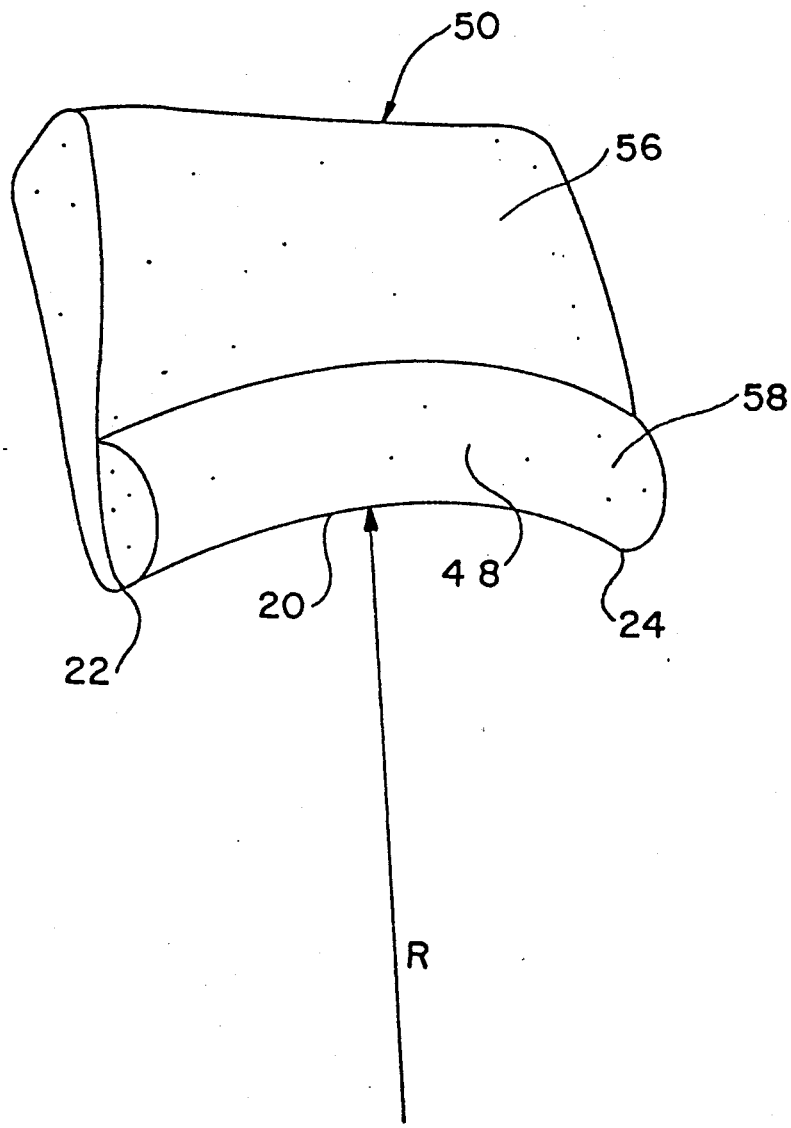
FIGS. 3A-3D represent perspective views of other embodiments of pillows of the present invention.
Figure 3B:
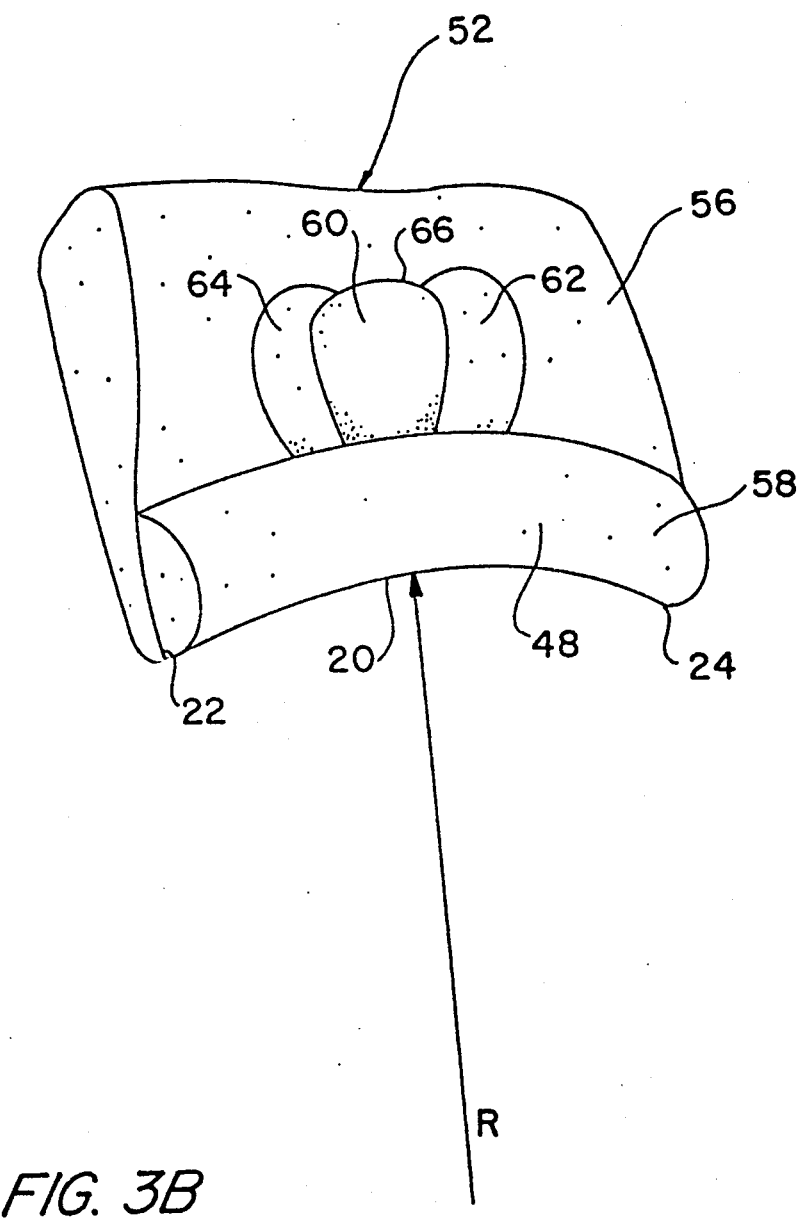

FIGS. 3A-3D illustrate different embodiments of pillows 50, 52, 54 and 55 which prevent or reduce snoring of a sleeping individual. Each pillow 50, 52, 54 and 55 is devoid of a convoluted material layer or surface as well as a scalloped bolster surface. Rather, pillows 50, 52, 54 and 55 comprise a base member 56 and an arcuate bolster 58 supported on the upper surface of the arcuate end of the base member. FIG. 3A illustrates an embodiment which does not have a depression area formed in the upper surface of base member 56 for receiving the head of the sleeper. FIG. 3B, on the other hand, illustrates a pillow which has a depression area 60 which includes a central depression 66 and shallower left and right side depressions 62 and 64. Central depression 62 is adapted to conform to the back of the user's head much like depression 38 of FIG. 2. Side depressions 62 and 64 share a boundary with central depression 62 and are adapted to conform to the side of a user's face when in a side sleeping position (FIG. 5) and yet provide proper positioning of the head.

Figure 3C:
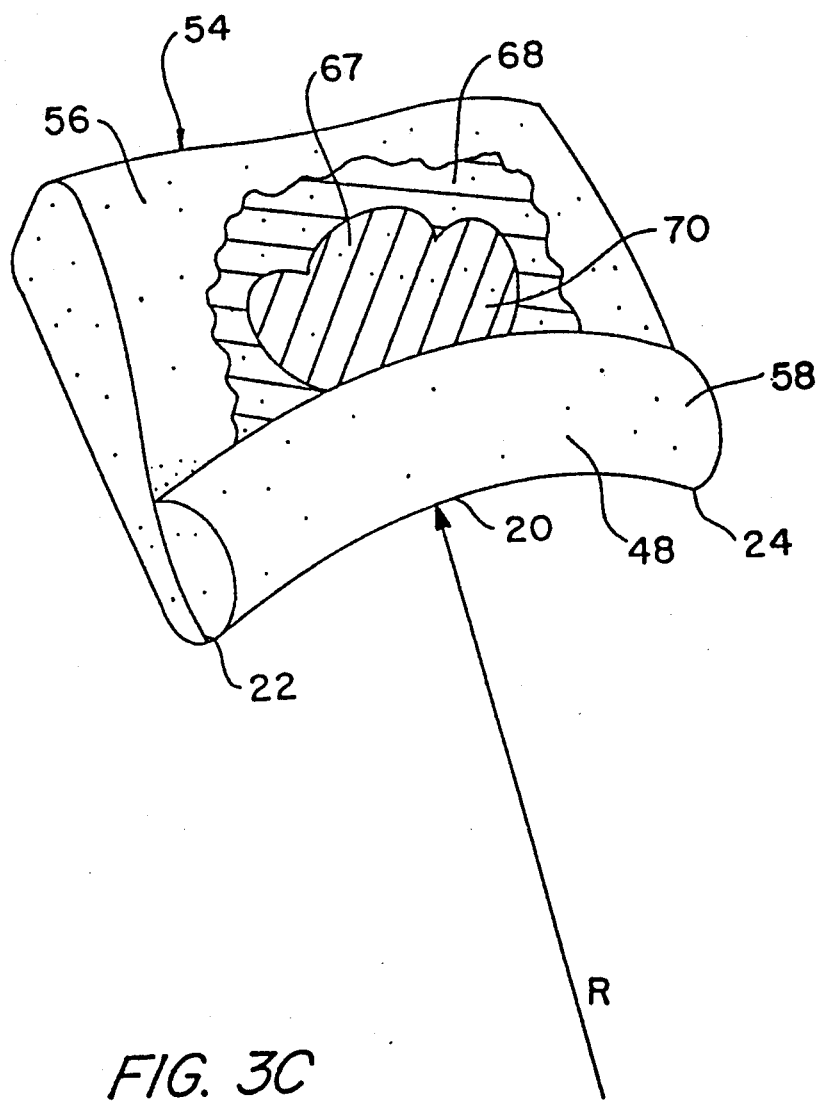
Figure 4:
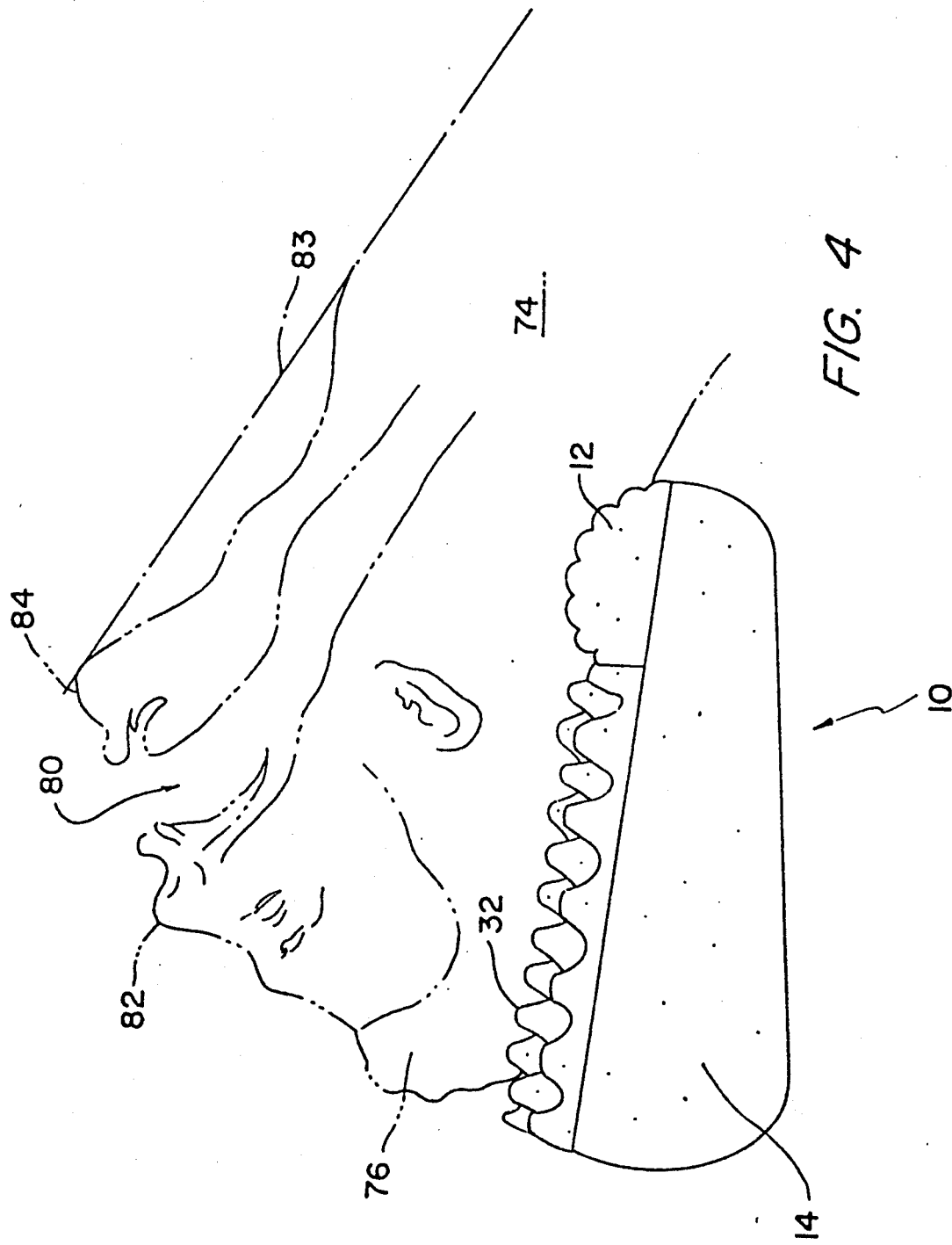
FIG. 4 represents a side view of one embodiment of the invention as well as the position of the head and neck of a user in a back sleeping position.

FIG. 3C illustrates an embodiment where rather than having depressions being formed in the upper surface of base member 56, a different type of material is utilized in forming a central region 67. The cut out portion of region 67 has a first material 68 and a second material 70 being used to form the central area. Depending on the type of materials being utilized to form the base member and the central area, it is possible to have a different firmness value for each of the materials. Preferably, the material 70 in central area 67 is a high quality cellular polyurethane material having a high density and being lower in initial firmness in order to position the head of the user in a manner which is optimal, as described above, and thus reduce, and even prevent, snoring by the user when asleep.

Figure 3D:
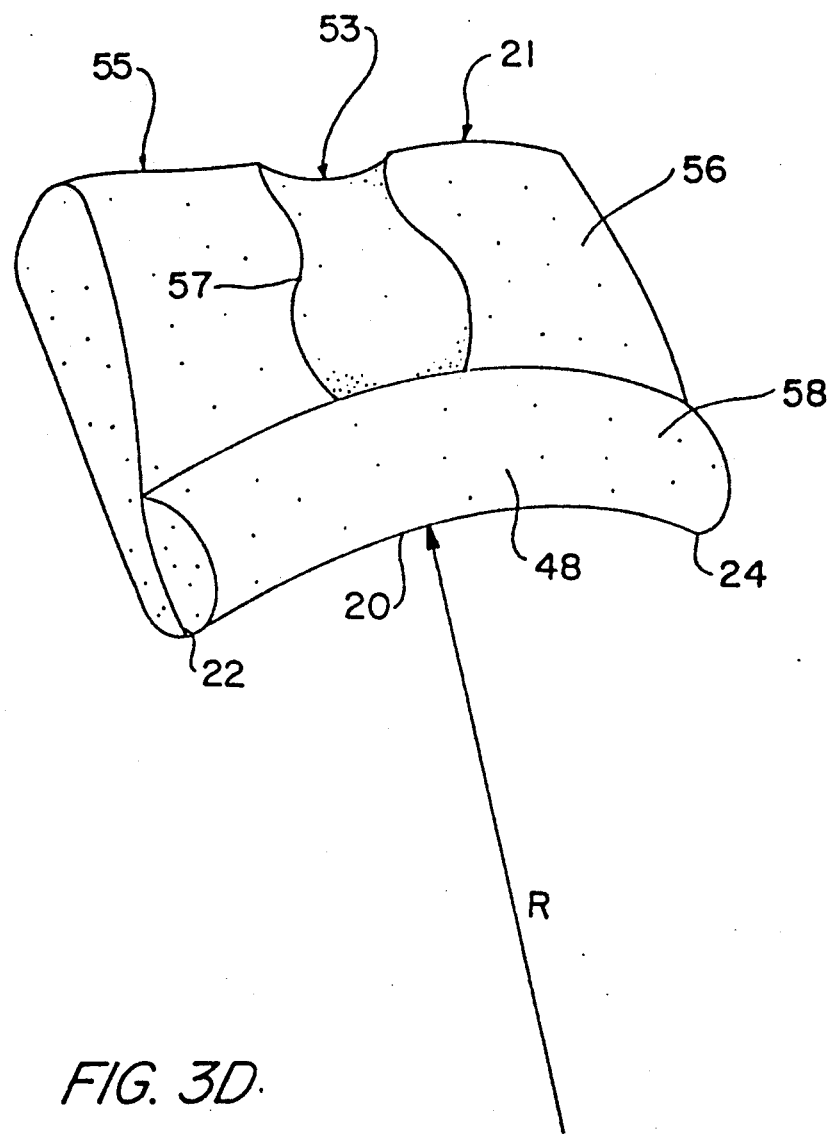
Figure 7:
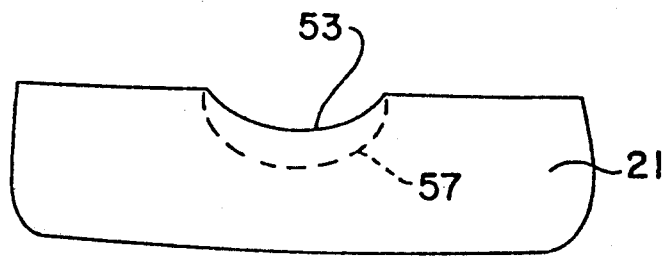
FIG. 7 represents a side view of the rear edge of the pillow illustrated in FIG. 3D.

FIG. 3D illustrates still another embodiment of the pillow of the invention wherein the depression 57 formed in the central portion of the pillow extends to the rear edge 21. This extension of the depression results in the formation of a depression 53 as illustrated in FIGS. 3 and 7. The depression 53 provides an added advantage to the pillow of the present invention by making it further adjustable to a person's body shape and preferences. Thus the depression 53 at the back edge of the pillow, which is shallower than the central depression 57, as seen in FIG. 7, provides an optimal air passageway for the user. The depression 53 preferably narrows as it extends towards the rear edge of the pillow as shown in FIG. 3D. It is to be understood that the head supporting areas of the pillows illustrated in FIGS. 3B, 3C and 3D are depressions having the same characteristics and features as the depressions in the pillows illustrated in FIGS. 1, 2 and 5. Furthermore, it is also contemplated that a convoluted surface which follows the contours of the upper surface can be formed in or added to the upper surface of the base member.

Figures 6A, 6B, 6C:
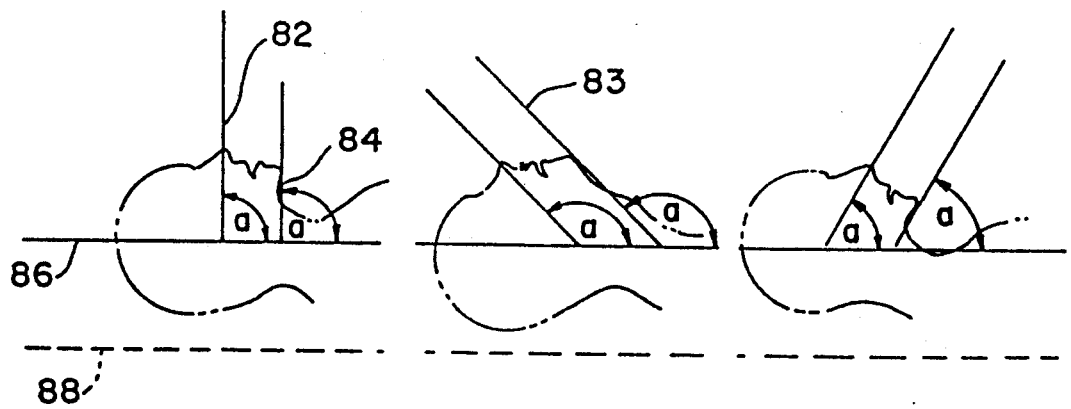
FIGS. 6A-6C represent various sleeping positions of a person's head.

As noted previously, it is important in achieving an effective anti-snoring pillow or a pillow which substantially reduces snoring, that the breathing passageways of a user be maintained as clear as possible. This is shown in FIG. 4 where a user 74 has his head 76, nose passageway 78, and mouth passageway 80 positioned on the pillow of the invention so as to minimize or prevent snoring when asleep. FIGS. 6A-6C illustrate various possible positions in which a user can have his head placed on a pillow. FIG. 6B schematically illustrates the extended or "sniffing" position in which the user has an optimal breathing passageway. As can be seen in FIG. 6B and FIG. 4, the tip of the nose 82 of the user as well as the chin 84 are positioned such that a plane 83 passing generally along the bottom surface of the chin and generally parallel to the extended neck of the individual intersects the plane of the surface of the bed supporting the bottom of the pillow at angle "a" from the horizontal and angle "a" is an obtuse angle.

It should be noted though that if the angle "a" becomes too large then partial blockage of the breathing passages begins to occur.

FIG. 6A illustrates, schematically, a head positioned in a manner whereby angle "a" is about 90. This position of the head does not provide the clear breathing passageway as the position shown in FIG. 6B, and, accordingly partial blockage of the breathing passages begins to occur, causing the individual to snore when asleep.

FIG. 6C illustrates, schematically, the head tilted towards the chest of the user. Angle "a" thus becomes an acute angle. If angle "a" becomes too small, the head is placed in a position which again leads to partial blockage of the breathing passageways and to increased snoring by the sleeping individual.

The pillow of the present invention, as shown in FIG. 4, positions the head of a user in a back sleeping position in the extended position so that the breathing passageways are at an optimum open condition. It is further contemplated that a range of obtuse angles "a", as defined above would preferably vary from about 125° to 165° and even more preferably be in the order of about 155°.

FIG. 5 illustrates the pillow of the invention wherein the user 90 is in a side sleeping position with his head 46 nestled comfortably in pillow 10. As shown in dashed line the head 46 of the user is positioned at a height L2 from the bottom edge 92 of the pillow. Height L2 is contemplated to be within the same ranges as height L1 discussed with respect to the pillow shown in FIG. 2, namely, in a range of about 3 to 5 inches and, preferably, between 3.5 and 4 inches. Also height L2 will be less than the height from the bottom surface of the neck supported on the upper surface of the bolster to the bottom 92 of the pillow. Thus, if cellular polyurethane foams of different densities were used for both the base member 14 and the convoluted material layer 32, the firmness value would be such that the user's head 46 would act to compress the foam to the extent necessary to come within the preferred ranges of heights L1 and L2. For example, if a head of a person were to weigh 12 pounds and the ILD value of the foam used was 12, then a four inch thick combination of base member and convoluted material in the area of head contact would compress essentially about an inch thus leaving the head about 3 inches from the bottom edge 92, which height is within the preferred range for L1 and L2.

FIG. 5 also illustrates a pillow providing a head position which improves the clearness of the breathing passageways of the person sleeping on his side. In this position, the spine 94 of the user, shown schematically, is essentially parallel to the bottom surface 92 of the pillow 10. Again, it is important to avoid twisting of the neck when attempting to provide optimal breathing passageways. The proper head position of FIG. 5 for a side sleeper is such that a plane P which is parallel to the bottom surface 92 would pass through the tip of the user's nose 96 and the spine 94. The bolster 12 is of a height and firmness which is suitable for keeping the head in the position shown in FIG. 5. This is achieved by providing support in the cheek and chin area of the user such that there is no twisting T of the spinal column 94, head and neck of the person while sleeping. In addition, the bolster 12 acts like a neck brace in keeping the chin up and away from the clavicle area of the user.

The pillows of the present invention may be produced by various methods. For instance, the entire pillow 10 can be formed in a molding operation so as to be unitary and consisting essentially of the same material, such as a cellular polyurethane. Alternatively, an outer layer for the pillow could be manufactured, again by molding or the like, which, when filled with a fluid, either liquid or gaseous, would expand into the desired shape. In the preferred embodiment, the base member 14, convoluted material layer 32 and bolster 12 are separately formed of cellular polyurethane of different densities in individual molds. Thereafter, the bolster 12 is bonded by adhesive, heat or the like to the upper front edge area of the base member 14. Also, the convoluted material layer 32 of cellular polyurethane foam with the "hills and valleys" can be laminated to the rest of the upper surface of the base member 14.

If a depression for supporting the head of the sleeper is desired, such as in the preferred embodiment, it can be formed either directly by molding or indirectly by pressure cutting a depression out of the upper surface of the base member 14. The convoluted layer 32 of substantially uniform thickness is then adhesively secured to the upper surface of the base member 14 and such layer assumes the configuration of such upper surface, including the depressed areas, such as the depression 38, to form the final pillow, as illustrated in FIGS. 1 and 2 of the drawing. Moreover, to achieve the longitudinal curve in the bolster, a moon shaped section is cut from the front edge of the base member 14 and the semi-circular or semi-hemispherical bolster 12 is adhesively adhered to the upper cutout surface of the base member 14, such that the outermost edge of the bolster coincides with the outermost front edge of the cut out base member. To complete the operation, the front edge corners of the base member would need to be cut off to conform with the bend ends of the bolster.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. An anti-snoring pillow for lessening the degree of blockage in a breathing passageway of a user of the pillow, comprising:

a base member having a front edge, a rear edge and a bottom and upper surface;

an elongated bolster, which provides support to the neck of the user and has a cross-sectional portion which is curved, said bolster being supported by said base member and said bolster being positioned closer to the front edge than said rear edge, and said rear edge being about 2 to 5 times higher than said front edge such that said upper surface slopes downward from said rear edge towards said front edge, said upper surface having a depression formed therein formed rearward of said bolster and said depression having a depth of between 1.0 to 4.0 inches, said bolster extending off of the upper surface of said base member for about 1.5 to 4.0 inches and being of a material higher in density and lower initial ILD value than said base member, and wherein said base member, said bolster, and said depression, in combination, are dimensioned and arranged such that, when a user, having a head weight between 10 to 14 pounds, is in a supine position and the neck of the user is firmly supported by said bolster, an angle of between about 125° to 165° is formed between a plane passing along the lower, essentially planar surface of the mandible of the user and a horizontal plane lying on the chest of the user.

2. An anti-snoring pillow as recited in claim 1 wherein the height said bolster extends off of said base is greater than the depth of the depression formed in said base.

3. An anti-snoring pillow as recited in claim 1 wherein said rear edge is higher than the maximum height of both said bolster and underlying base member in combination.

4. An anti-snoring pillow as recited in claim 1, wherein said obtuse angle is about 155°.

5. An anti-snoring pillow as recited in claim 1 wherein said bolster is semi-circular in cross-section with the uncurved portion of the semi-circular bolster being in contact with the upper surface of said base member.

6. An anti-snoring pillow as recited in claim 1 where said front edge is curved and said bolster is curved along its length to conform to the curvature of said front edge, and the forward most portion of said bolster is as far forward as the front edge of said base member.

7. An anti-snoring pillow as recited in claim 6 wherein the radius of the lengthwise curve of said bolster is in the range of about 1.5 to 3 feet.

8. An anti-snoring pillow as recited in claim 1 wherein said bolster is scalloped in cross-section so as to have a plurality of ridges extending along the length of said bolster and grooved recesses between said plurality of ridges.

9. An anti-snoring pillow as recited in claim 1 wherein the upper surface of said base member, except for that portion covered by said bolster, is convoluted.

10. An anti-snoring pillow as recited in claim 1 further comprising a layer of convoluted material which is laminated to the upper surface.

11. An anti-snoring pillow as recited in claim 1 wherein said pillow is formed of at least one type of polyurethane foam.

12. An anti-snoring pillow as recited in claim 11 wherein said base member is comprised of a material having an initial firmness value greater than said bolster.

13. An anti-snoring pillow as recited in claim 11 wherein said bolster is formed of polyurethane foam having an initial firmness ILD value of about 11 and said base member is also formed of polyurethane foam having a firmness value of about 16.

14. An anti-snoring pillow as recited in claim 1 wherein said front edge of said base member is curved inwardly toward the rear edge and said bolster is curved along its length to conform to the curvature of said front edge, and a forward most portion of said bolster is as far forward as the front edge of said base member.

15. An anti-snoring pillow as recited in claim 1 wherein said upper surface has a depression formed therein in a central region of said upper surface, said depression having a forward boundary positioned just rearward of a portion of the bolster which is closest to the rear edge of said base member, and said depression having a deepest point which is of less height from the bottom surface of said base member than is the lowest point of said bolster.

16. An anti-snoring pillow as recited in claim 15 further comprising a laminated layer of convoluted material secured to said upper surface.

17. An anti-snoring pillow as recited in claim 16 wherein said depression has a three-petal configuration which includes a central and two side sections, said central section being adapted to conform to a back of a head of the user and said side sections adapted to conform to a side of the head of a user.

18. An anti-snoring pillow as recited in claim 1 wherein said base member has a central area formed of a different material which has a different firmness and density value than the rest of said base member such that an added degree of comfort is provided the user.

19. An anti-snoring pillow as recited in claim 1 wherein a depression is formed in the upper surface of said base member which extends to the rear edge of the base member thereby forming a neck slot in said rear edge.

20. An anti-snoring pillow, comprising:
a compressible base member having a front edge, a rear edge and a bottom and upper surface, said front edge having a central portion and two end portions and said front edge being curved such that the central portion of said front edge is closer to the rear edge of said base member than the two end portions of said front edge, and said rear edge having a vertical height which is greater than said front edge, said lower surface being essentially planar and said upper surface sloping downward from said rear edge towards said front edge of said base member; and an elongated, compressible bolster which is positioned closer to the front edge of said base member than to said rear edge, said bolster having a cross-sectional exterior portion which is curved and said bolster being curved lengthwise so as to have essentially the same amount of curvature as that of the lengthwise curve of the front edge of said base member; and said pillow being formed of at least two different types of polyurethane foam with said base member being comprised of a material having an initial ILD firmness value greater than said bolster and said bolster being formed of a material of a higher density than said base member such that, in a region of 25% compression or more for both said base member and bolster, the ILD firmness value of said bolster becomes greater than that of said base member.

21. An anti-snoring pillow as recited in claim 1, wherein said obtuse angle is in a range of about 125° to 165°.

22. An anti-snoring pillow as recited in claim 20, wherein said obtuse angle is about 155°.

23. An anti-snoring pillow having an upper and a lower surface, comprising:
a compressible base member having a front edge and a rear edge, and the upper surface of said pillow having a depression formed in a central region of said base member which is about 1 to 4 inches deep;
a compressible bolster secured to said base member and positioned forward of said depression, said bolster having a height which is about from 1.5 inches to 4 inches; and
said pillow being formed of at least two different types of polyurethane foam with said base member being comprised of a material having an initial ILD firmness value greater than that of said bolster and said bolster being formed of a material of a higher density than that of said base member.

24. An anti-snoring pillow as recited in claim 23 wherein said higher density bolster material results in the ILD value for said bolster becoming greater than that of said base member upon 25% compression or more of said bolster.

25. An anti-snoring pillow as recited in claim 23 wherein said bolster and said base member are dimensioned and arranged such that an angle between about 125° to 165° is formed between a plane passing along the lower, essentially planar surface of the mandible of a user in a supine position and a horizontal plane lying on the chest of the user.

26. An anti-snoring pillow as recited in claim 23 wherein the initial ILD value of said base member falls between about 10 to 21.

27. An anti-snoring pillow as recited in claim 23 wherein the initial ILD value for said base member is between about 16 to 18.

28. An anti-snoring pillow as recited in claim 23 wherein said bolster has a bottom area which is in contact with said base member and is higher than the portion of the upper surface of said pillow defining the deepest portion of said depression when said pillow is in a non-compressed state.

29. An anti-snoring pillow having an upper and a bottom surface, comprising:
a polyurethane base member having a forward edge and a rearward edge and an upper surface, said forward edge being lower than said rear edge such that the upper surface of said base slopes downwardly from said rear edge to said front edge, said base member having an initial ILD value between about 10 to 21, and said forward edge having a mid-region and two end regions with the mid region closer to said rear edge than said two end regions,
a polyurethane bolster supported by said base member, said bolster extending off of said base member for about 1.5 to 5 inches and said bolster formed of a material having a higher density and having a lower initial ILD value than that of said base member,
said pillow having a depression formed therein in a central region of said pillow and rearward of said bolster, the depression in said pillow having a depth from between about 1 to 4 inches.

30. An anti-snoring pillow as recited in claim 29 wherein said higher density bolster material results in the ILD value for said bolster becoming greater than that of said base member upon a compression of 25% or more of said bolster.

31. An anti-snoring pillow as recited in claim 26 wherein said base member, said bolster and said depression, in combination, are dimensioned and arranged such that, when a user, having a head weight between 10 to 14 pounds, is in a supine position and the neck of the user is firmly supported by said bolster, an angle of between about 125° to 165° is formed between a plane passing along the lower, essentially planar surface of the mandible of the user and a horizontal plane lying on the chest of the user.

32. An anti-snoring pillow as recited in claim 29 wherein said bolster has a bottom area which is in contact with said base member and is higher than the portion of the upper surface of said pillow defining the deepest portion of said depression when said pillow is in a non-compressed state.

33. An anti-snoring pillow having an upper and a lower surface, comprising:
a compressible base member having a front edge and a rear edge, and the upper surface of said pillow, in a central region of said base member, having a depression formed therein which is about 1 to 4 inches deep;
a compressible bolster secured to said base member at a position forward of said depression, said bolster having a height which is about from 1.5 to 4 inches and said bolster formed of a material having a higher density and a lower initial ILD value than that of said base member,
said pillow being formed of at least two different types of polyurethane foam with said base member formed of one type of foam and said bolster formed of another type of foam; and
said bolster having a bottom surface with is in contact with said base member and is higher than the portion of the upper surface of said pillow defining the deepest portion of said depression when said pillow is in a non-compressed state.

34. An anti-snoring pillow as recited in claim 33 wherein said bolster, base member and depression are arranged such that, when a user is firmly supported by said pillow and said pillow compressed, the portion of the upper surface of said pillow defining the deepest portion of said depression is lower than said bottom surface of said bolster.

* * * * *